US010292627B2

(12) United States Patent
Riekkinen

(10) Patent No.: US 10,292,627 B2
(45) Date of Patent: May 21, 2019

(54) METHOD AND APPARATUS FOR NONINVASIVE DETECTION OF POTENTIAL SYMPTOMLESS BLOOD LOSS

(71) Applicant: Heikki Veli Juhani Riekkinen, Kuopio (FI)

(72) Inventor: Heikki Veli Juhani Riekkinen, Kuopio (FI)

( * ) Notice: Subject to any disclaimer, the term of this patent is extended or adjusted under 35 U.S.C. 154(b) by 0 days.

(21) Appl. No.: 15/794,893

(22) Filed: Oct. 26, 2017

(65) Prior Publication Data

US 2018/0110447 A1 Apr. 26, 2018

(30) Foreign Application Priority Data

Oct. 26, 2016 (FI) ...................................... 20165811

(51) Int. Cl.
*A61B 5/145* (2006.01)
*A61B 5/00* (2006.01)
(Continued)

(52) U.S. Cl.
CPC ............ *A61B 5/145* (2013.01); *A61B 5/0006* (2013.01); *A61B 5/021* (2013.01);
(Continued)

(58) Field of Classification Search
CPC ... A61B 5/0205; A61B 5/0402; A61B 5/7275; A61B 5/7282; A61B 5/0245; A61B 5/0452; A61B 5/0006; A61B 5/04012; A61B 5/746; A61B 5/0456; A61B 5/486; A61B 5/4875; A61B 5/145; A61B 5/0408;
(Continued)

(56) References Cited

U.S. PATENT DOCUMENTS

2007/0112275 A1 5/2007 Cooke et al.
2008/0287753 A1 11/2008 Parlikar et al.
2014/0187990 A1 7/2014 Banet et al.

FOREIGN PATENT DOCUMENTS

RU 2365328 C1 8/2009
WO 2004/082460 A2 9/2004
(Continued)

OTHER PUBLICATIONS

Feb. 6, 2017 Search Report issued in Finnish Patent Application No. 20165811.
(Continued)

*Primary Examiner* — Deborah L Malamud
(74) *Attorney, Agent, or Firm* — Oliff PLC

(57) ABSTRACT

A method including obtaining a first electrocardiography ["ECG"] reading from a test subject when the test subject is believed to not suffer from blood volume loss and obtaining a second ECG reading from the test subject when the test subject is in an unknown condition regarding blood volume loss. The first ECG reading and the second ECG reading are obtained using the same electrode positions on the test subject and include sets of ECG signals which, based on experimental data, respond to small decrease in blood volume by a statistically significant strength decrease. If the second ECG reading exhibits a statistically significant strength decrease compared with the first ECG reading, an alert condition is raised, which indicates potential small decrease in blood volume. The method can be embodied as a stand-alone ECG apparatus or as an add-on unit to an ECG apparatus.

7 Claims, 4 Drawing Sheets

(51) Int. Cl.
*A61B 5/021* (2006.01)
*A61B 5/0402* (2006.01)
*A61B 5/02* (2006.01)
*A61B 5/0452* (2006.01)
*A61B 5/0245* (2006.01)

(52) U.S. Cl.
CPC ...... *A61B 5/02042* (2013.01); *A61B 5/04023* (2013.01); *A61B 5/0452* (2013.01); *A61B 5/0245* (2013.01)

(58) Field of Classification Search
CPC ..... A61B 5/4869; A61B 5/02; A61B 5/02028; A61B 5/0004; A61B 5/0468; A61B 5/72; A61H 2230/04
See application file for complete search history.

(56) References Cited

FOREIGN PATENT DOCUMENTS

| WO | 2008/055173 A2 | 5/2008 |
|---|---|---|
| WO | 2010/077997 A2 | 7/2010 |

OTHER PUBLICATIONS

Rudy et al., "Comments on the Effect of Variations in the Size of the Heart on the Magnitude of ECG Potentials", J. Electrocardiology, vol. 13, pp. 79-82, 1980.
Plisek et al., "Elektrokardiographische Veränderungen nach akutem Blutverlust bei Kaninchen", pp. 181-195, 1969.
Nelson et al., "Magnitude and Location of a Dipole in a Circular Ring With Non-Insulating Boundaries", J. Electrocardiology, vol. 19, pp. 347-353, 1986.
Brody Daniel, "A Theoretical Analysis of Intracavitary Blood Mass Influence on the Heart-Lead Relationship", Circulation Research, Journal of the American Heart Association, vol. 4, pp. 731-738, 1956.
Vancheri et al., "Relationship of QRS amplitude to left ventricular dimensions after acute blood volume reduction in normal subjects", European Heart Journal, vol. 10, pp. 341-345, 1989.
Manoach et al., "Influence of hemorrhage on the QRS complex of the electrocardiogram", American Heart Journal, vol. 82, pp. 55-61, 1971.
Ishikawa et al., "Influence of peripheral intravenous contrast injection on the QRS complex in healthy men", Cardiovascular Research, vol. 20, pp. 61-66, 1986.
Ishikawa et al., "Electrocardiographic changes due to sauna bathing Influence of acute reduction in circulating blood volume on body surface potentials with special reference to the Brody effect", vol. 50, pp. 469-475, 1983.
Hoberg et al., "Verhalten der R-Amplituden-Höhe bei Änderung des linksventrikularen Volumens von Herzgesunden". Kardiologie, vol. 71, pp. 544-547, 1982.
Feldman et al., "Relation of Electrocardiographic R-Wave Amplitude to Changes in Left Ventricular Chamber Size and Position in Normal Subjects", Miscellaneous Topics, vol. 55, pp. 1168-1174, 1985.
Della Torre et al., "Effect of acute hemorrhage on QRS amplitude of the lead II canine electrocardiogram", vol. 77, pp. 298-300, 1999.
Castini et al., "Demonstration of the Relationship Between Heart Dimensions and QRS Voltage Amplitude", Journal of Electrocardiology, vol. 29, pp. 169-173. 1996.
Amoore et al., "The Effect of Variations of Ventricular Volume on the Electrocardiogram. A Comparison of Two Model Simulations", Journal of Electrocardiology, vol. 21, pp. 154-160, 1988.
Sokolow et al., "The Ventricular Complex in left Ventricular Hypertrophy as obtained by Unipolar Precordial and Limb Leads", American Heart Journal, vol. 37, pp. 161-186, 1949.
Rautaharju et al, "A Standardized Procedure for Locating and Documenting ECG Chest Electrode Positions", Journal of Electrocardiology, vol. 31, pp. 17-29, 1998.
McManus et al., "R-wave Amplitude in Lead II of an Electrocardiograph Correlates with Central Hypovolemia in Human Beings", Basic Investigations, pp. 1003-1010, 2006.
Lepeschkin et al., "The Measurement of the Q-T Interval of the Electrocardiogram", Circulation, vol. 6, pp. 378-388, 1952.
Hall, "Guyton and Hall Textbook of Medical Physiology", 12th ed., pp. 134-135, 2011.
Gubner et al., "Electrocardiographic Criteria of Left Ventricular Hypertrophy", Archives of Internal Medicine, pp. 196-209, 1943.
Feldman et al., "Change in ventricular cavity size: differential effects on QRS and T wave amplitude", Circulation, vol. 72, pp. 495-501, 1985.
Casale et al., "Electrocardiographic Detection of Left Ventricular Hypertrophy: Development and Prospective Validation of Improved Criteria", The American College of Cardiology, vol. 6, pp. 572-580.
H.G. Bazett, "An Analysis of the Time-Relations of Electrocardiograms", History of Electrocardiology, vol. 2, pp. 177-194, 1997.
Van Den Halogen et al., "Reproducibility of electrocardiographic criteria for left ventricular hypertrophy in hypertensive patients in general practice", European Heart Journal, vol. 13, pp. 1606-1610, 1992.
Smit et al., "Effects of breath-holding position on the QRS amplitudes in the routine electrocardiogram", Journal of Electrocardiology, vol. 42, pp. 400-404, 2009.
McLaughlin et al., "The value of the coefficient of variation in assessing repeat variation in ECG measurements", European Heart Journal, vol. 19, pp. 342-351, 1998.
John E. Madias, "Manual-based versus automation-based measurements of the amplitude of QRS complexes and T waves in patients with changing edematous states: clinical implications", Journal of Electrocardiology, vol. 41, pp. 15-18, 2008.
Madias et al., "Anasarca-Mediated Attenuation of the Amplitude of Electrocardiogram Complexes: A Description of a Heretofore Unrecognized Phenomenon", Journal of the American College of Cardiology, vol. 38, pp. 756-764, 2001.
Hall, "Guyton and Hall Textbook of Medical Physiology", 12th ed., pp. 274, 2011.
Farb et al., "Day-to-Day Variability of Voltage Measurements Used in Electrocardiographic Criteria for Left Ventricular Hypertrophy", vol. 15, pp. 618-623, 1990.
Angeli F et al., "Day-to-Day variability of electrocardiographic diagnosis of left ventricular hypertrophy in hypertensive patients. Influence of electrode placement", J. Cardiovasc. Med., vol. 7, pp. 812-816, (Abstract Only).

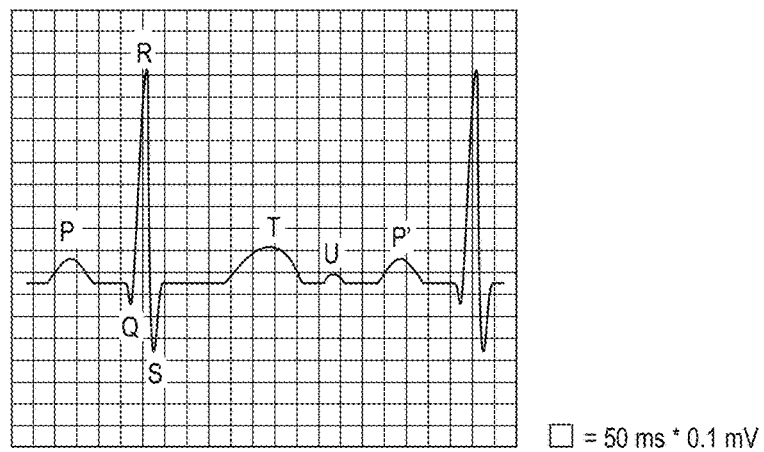
Fig. 1
(Prior art)
☐ = 50 ms * 0.1 mV
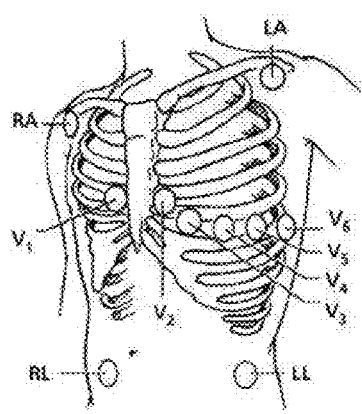
Fig. 2
(Prior art)
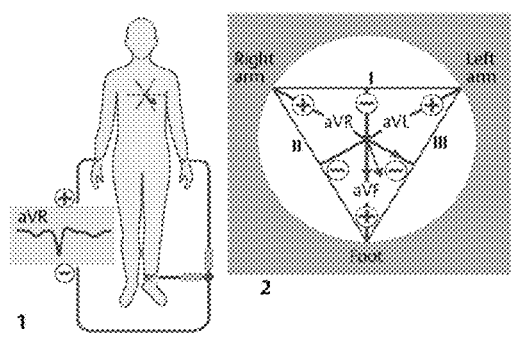

METHOD AND APPARATUS FOR NONINVASIVE DETECTION OF POTENTIAL SYMPTOMLESS BLOOD LOSS

FIELD

The present invention relates to methods and apparatuses for detection of a blood volume decrease. More particularly, the present invention relates to a method and apparatus for noninvasive monitoring of small postoperative blood volume decrease using ECG amplitudes that change significantly after blood volume changes.

BACKGROUND

During a surgical operation it is usually easy to measure the extent of blood loss and to compensate it. So, at the end of the operation the blood volume of a person is normal. After every operation there is, depending on the state and medication of the patient and the type of the operation, at least some blood loss. Mostly this blood loss is so slight that no actions are needed. Postoperatively, in the recovery room, it is not easy to estimate a possible decrease in blood volume. At present, in most recovery rooms, a nurse measures the blood pressure and the heart rate of the patient for instance every 15 minutes. This takes quite a lot of time, and more personnel are needed. On the other hand, it is well known that blood pressure and heart rate are normal when the blood volume loss is not more than 10 percent of the normal blood volume. About 10 percent of the total blood volume of a person may be removed with almost no effect on either arterial pressure or cardiac output. In blood donation, about 500 ml of blood is removed with no harm to the donor. For a man weighing 70 kg this means 10 percent of his total blood volume. It is desirable to detect a blood loss condition while still in the early stage, because such an early detection would give hospital personnel more time to take corrective action. A problem is, however, that there is virtually nothing that would serve as an indicator of such early stage of blood loss.

Brody (1) published in 1956 a theoretical analysis postulating that the relatively large conductivity of the intracavitary blood mass augments the radial components of myocardial doublets. Published studies supporting the theory of Brody have been based on mathematical models (2-3), experimental animal investigations (4-6) and clinical studies (7-9). On the other hand, mathematical models (10), and clinical investigations (11-14) have shown an inverse relationship between ventricular volume and electrical voltage.

In animal experiments, withdrawal of blood has been used to modify cardiac volumes (4-6). In humans Valsalva maneuver (8-9), infusion of drugs (8, 13), sauna bathing (11), pressure cuffs around the limbs (7) and lower body negative pressure (14) have been used. Studies of the quantitative effects of acute hemorrhage on QRS and T wave amplitudes in humans was not found in recent literature.

Intensive experimental work to develop methods for noninvasive detecting a decrease in blood volume has been made from the beginning of the twentieth century.

Many physiological measurements have been used for detecting blood volume changes including impedance changes, an electrocardiogram, a photoplethysmogram and oxygen saturation, respiratory, skin temperature and blood pressure measurements.

ECG changes exist always, if the decrease of blood volume is large. Unfortunately, the situation of the patient is already serious when ECG changes occur. Therefore, ECG changes occurring after smaller decrease of blood volume have not been looked for. Heart rate variability (HRV) that is dependent on the autonomic nervous system and not specific for blood volume is one of the most used ECG measurements. Studies using ECG amplitude measurements have been rare. No T wave or chest lead amplitude changes have been used. The probable reason for this is that reliance on chest lead amplitude measurements has been criticized because of great variations in serial measurements depending on non-standardized placement of chest electrodes (16). Also lower body negative pressure (LBNP), used in most studies to simulate decrease of central blood volume, can change ECG amplitudes by changing position of the heart and reducing the electrical conductivity of upper body by causing fluid shift from upper to lower body.

Another popular measurement for predicting blood volume changes has been blood pressure curve using photoplethysmogram. This measurement is partly dependent on left ventricular end-diastolic volume (preload), which reflects blood volume. It is, however, also dependent on the resistance of circulation (afterload). For instance the tone of autonomic nervous system, possible stenoses in arteries and position of the upper arm (if the probe is on a finger) acts on the resistance of circulation.

In most prior experiments LBNP has been used to simulate decreased central blood volume. The reason for this is that the ability to experimentally study the effects of blood volume decrease is currently limited to human studies in which blood loss is induced by voluntary blood donation. Members of US Army Institute of Surgical Research wrote in an article: "In the case of human blood donation, the removal of only small percentages of total blood volume is easily compensated for in most cases and does not provide predictions as to the point at which blood pressure decompensation will occur with greater volumes of blood loss" (Cooke W, Ryan K, Convertino A. Lower body negative pressure as a model to study progression to acute hemorrhagic shock in humans. J Appl Physiol 2004; 96: 1249-61). For the above reason the blood volume decrease in experiments using LBNP has been 15-20 percent or more in about 75 percent of test subjects.

Prior methods are relatively complicated using several different measurements and devices which raise the costs of the method.

A problem underlying the invention is related to the difficulty of detecting small decrease of blood volume. Currently there is no easy and noninvasive method to measure small changes of blood volume.

SUMMARY

An object of the invention is to develop non-invasive methods and apparatuses for early detection of potential small decrease in blood volume. Aspects of the invention include a method and an apparatus according to the respective independent claims.

The invention is based, at least partially, to the inventor's hypothesis, according to which in acute blood volume loss, T wave amplitudes and T/R amplitude ratios in humans decrease earlier than QRS amplitudes do. This hypothesis was studied and confirmed in a study of the quantitative influence of acute blood volume loss on QRS and T wave amplitudes and T/R amplitude ratios. As part of this study, an electrocardiogram apparatus was used to record a twelve-lead electrocardiogram (ECG) in normal, healthy men, before and after a blood donation of 500 ml.

Although the relationship between ventricular volume and QRS amplitudes have been investigated in many studies, there are not many studies examining changes in T wave amplitudes or T/R amplitude ratios. In the study of Feldman et al (15), after Valsalva maneuver relative decreases of mean T wave amplitude and T/R amplitude ratio in humans were greater than relative R wave amplitude decreases in leads V5 and V6. In hindsight, the fact that T wave amplitudes and T/R amplitude ratios exhibit similar changes in Valsalva maneuver and bleeding-induced symptomless blood loss appears to support the hypothesis of the inventor.

The method and apparatus enables the provision of easy and noninvasive monitoring also relatively small (10% or less) postoperative blood volume decrease in a person based on measurements of repolarization amplitude (T wave) of the heart, wherein T and R wave amplitudes, using standardized electrode placement, are measured. T wave amplitude is expressed in percentage of the amplitude at the beginning of the postoperative monitoring. Based on experimental data, 7 microvolt decrease in amplitude corresponds to 1% decrease in blood volume. Every 5% decrease in blood volume raises an alert condition. The method and apparatus enables providing the nurse of the postoperative recovery room with information so that the nurse is able to oversee the condition of the patient. The nurse has more time for the other care of the patients, and may be less nurses are needed in the recovery room.

BRIEF DESCRIPTION OF THE DRAWINGS

In the following sections, specific embodiments of the invention and research work underlying the invention will be described in greater detail in connection with illustrative but non-restrictive examples. A reference is made to the following drawings:

FIG. 1 schematically shows a typical composite ECG waveform, which comprises P, Q, R, S, T and U waves;

FIG. 2 illustrates the notations used to refer to electrode placement;

DETAILED DESCRIPTION OF SOME SPECIFIC EMBODIMENTS

Figure 3:
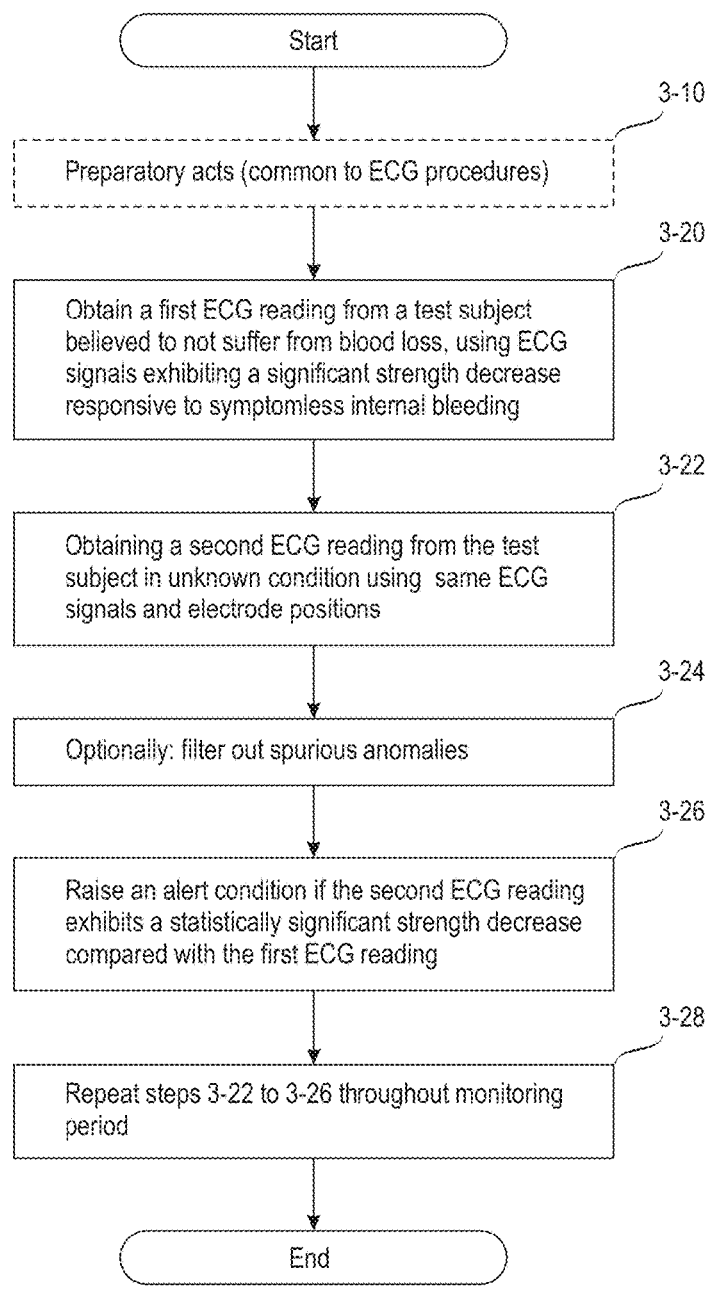
FIG. 3 illustrates an embodiment of the inventive method.

The present invention discloses an easy and noninvasive method and apparatus for detection of also small (10% or less) reductions in blood volume of postoperative patients.

It has been shown that a major determinant of the amplitude of T wave, caused by repolarisation of the heart, is left ventricular cavity size (15) which is directly dependent of left ventricular end-diastolic volume, reflecting blood volume.

In the study of Feldman et al (15), the volume of left ventricle of heart decreased after Valsalva manoeuvre about 30 percent, and the amplitude of lead V5 T wave 20 percent. Therefore it was hypothetized that using a standardized procedure for locating and documenting ECG chest electrode positions (16), it may be possible to find significant changes in R and T wave amplitudes of chest leads closest to the left ventricle of heart, also after relative small changes in blood volume. This hypothesis was studied and confirmed in a study of the quantitative influence of acute loss of blood volume of 500 ml on QRS and T wave amplitudes and T/R amplitude ratios. The most significant change (p<0.001) was found in the amplitude of T wave in lead V4, where the mean amplitude decreased from 0.47 mV to 0.41 mV. The median value of the confidence interval of the amplitude decrease was 60 µV. Corrected by the weight of the study persons, the mean decrease of TV4 amplitude, after removing of 10 percent of blood volume, was 70 µV. Thereby the estimated amplitude decrease corresponding one percent decrease in blood volume was 7 µV.

Electrocardiograph is one of the most usual and important medical devices in hospitals. Therefore in the present invention it was found to be practical and cost-effective to construct an ECG device that may be used as an electrocardiograph and, besides, detect changes in blood volume.

An exemplary device (apparatus) is an electrocardiograph with an internal add-on unit to measure a possible decrease in blood volume of postoperative patients.

T wave amplitude changes of lead V4, with standardized placement of electrodes, are used to evaluate blood volume changes. As discussed above, 7 µV decrease in TV4 amplitude corresponds to one percent decrease in blood volume, and this way 70 µV decrease in TV4 amplitude corresponds to ten percent decrease in postoperative blood volume.

The device shows the blood volume on a screen in percentages of the blood volume at the beginning of the postoperative monitoring using measurements of TV4 wave amplitudes.

When the blood volume is over 90 percent, the nurse of the postoperative recovery room is able to detect that no actions are needed, and it is not necessary to measure the blood pressure. Then the nurse has more time for other care of the patients, and less nurses may be needed in the recovery room.

When the blood volume decreases to 90 percent, it does not necessarily mean that any actions are required. The nurse of the recovery room may, however, consider whether or not s/he should consult a doctor.

FIG. 1 schematically shows a typical composite ECG waveform, which comprises P, Q, R, S, T and U waves. The purpose of FIG. 1 is not to give detailed instructions concerning electrode placement, which is well known in the art, but instead to clarify the notations being used.

FIG. 2 illustrates the notations used to refer to electrode placement. There are six chest or precordial leads, V1 through V6, whose placement is based on anatomical landmarks.

In addition to the above-mentioned leads, which are unipolar, there are three bipolar leads, namely:

Lead I: RA (−) to LA (+) (Right Left, or lateral),
Lead II: RA (−) to LL (+) (Superior Inferior), and
Lead III: LA (−) to LL (+) (Superior Inferior).

Finally, there are three augmented unipolar limb leads on the frontal plane, namely:

Lead aVR: RA (+) to [LA & LL] (−) (Rightward),
Lead aVL: LA (+) to [RA & LL] (−) (Leftward), and
Lead aVF: LL (+) to [RA & LA] (−) (Inferior).

A combination of wave x and lead y refers to measurement of wave x from lead y. For instance, "TV4" refers to measurement of wave T from lead V4, while "TV4/RV4" refers to the ratio of T wave and R wave in lead V4. LA, RA, LL and RL stand for left arm, right arm, left limb and right limb. These positions are not normally used in 12-lead ECG, but the notations LA, RA, LL and RL are used to describe the bipolar and augmented leads.

FIG. 3 illustrates an embodiment of the inventive method. Step 3-10 comprises preparatory acts, most of which are common to ECG procedures, such as preparing the test subject, who typically is a patient, and attaching the electrodes and ECG leads. Step 3-10 is shown in a dashed outline, which indicates the fact that such preparatory acts are not within the scope of an apparatus embodying aspects of the invention. A preferred departure from conventional ECG procedures is placement of the V4 lead, whose preferred position and placement technique are disclosed in reference (16).

Step 3-20 comprises obtaining a first ECG reading from a test subject when the test subject is believed to not suffer from blood loss. Step 3-22 comprises obtaining a second ECG reading from the test subject when the test subject is in an unknown condition regarding blood loss. The first ECG reading and the second ECG reading comprise sets of ECG signals which, based on experimental data, respond to symptomless internal bleeding by a statistically significant strength decrease. The first ECG reading and the second ECG reading are obtained using the same electrode positions on the test subject.

An optional step 3-24 comprises filtering out spurious anomalies. Strictly speaking, step 3-24 is not necessary, and the "Results" section of this document identifies multiple ECG signals which serve as statistically significant indicators of potential bleeding-induced blood loss even without additional filtering. The "Results" section further identifies candidate ECG signals, which do exhibit responses to blood loss, but do not meet the criteria of statistical significance. It is possible that further research, based on the scientific results published herein, reveal ECG signals which turn out to be statistically significant indicators after adequate filtering. For instance, such filtering techniques may comprises taking a statistically representative value (eg average, median, n:th percentile, or the like) from multiple readings, time hysteresis, and so on.

In step 3-26 an alert condition is raised if the second ECG reading exhibits a statistically significant strength decrease compared with the first ECG reading. Raising the alert condition typically involves causing emission of a visual and/or aural alert signal locally and/or remotely. For instance, a local alert signal is a signal detectable in the same site as the test subject, while a remote alert signal may be transmitted to a remote monitoring facility and/or to devices carried by personnel.

Finally, steps 3-22 to 3-26 may be repeated throughout a monitoring period, such as the duration of the early post-operative care.

Figure 4:
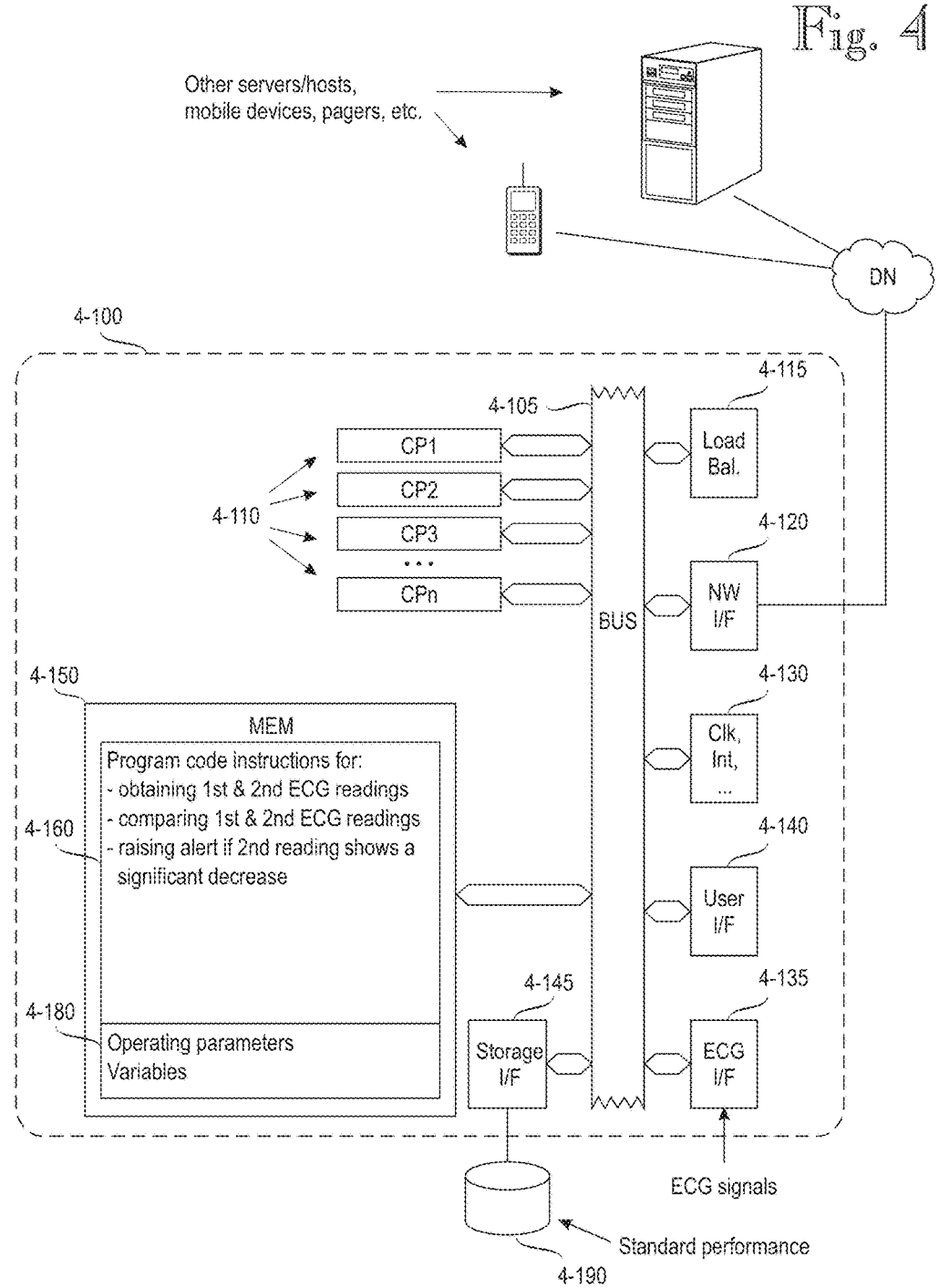
FIG. 4 schematically shows an apparatus for carrying out embodiments of the inventive method.

FIG. 4 schematically shows an ECG signal processor adapted for real-time detection of acute small blood volume decrease. An ECG signal processor adapted to implement the method of the invention can be embodied as a stand-alone unit or as an external or internal add-on unit to a conventional ECG apparatus. The description of FIG. 4 is based on the assumption that the inventive apparatus is embodied as external add-on unit to an ECG apparatus.

The architecture of the ECG signal processor, generally denoted by reference numeral 4-100, comprises one or more central processing units CP1 . . . CPn, generally denoted by reference numeral 4-110. Implementations comprising multiple processing units 4-110 are preferably provided with a load balancing unit 4-115 that balances processing load among the multiple processing units 4-110. The multiple processing units 4-110 may be implemented as separate processor components or as physical processor cores or virtual processors within a single component case. In a typical implementation the computer architecture 4-100 comprises a network interface 4-120 for communicating with various data networks, which are generally denoted by reference sign DN. The data networks DN may include wired or wireless local-area networks, and/or wide-area networks, such as the internet.

The ECG signal processor 4-100 may also comprise a local user interface 4-140. Depending on implementation, the user interface 4-140 may comprise local input-output circuitry for a local user interface, such as a keyboard, mouse and display (not shown). The computer architecture also comprises memory 4-150 for storing program instructions, operating parameters and variables. Reference numeral 4-160 denotes a program suite for the ECG signal processor. The program suite 4-160 comprises program code instructions for instructing the processor(s) 4-110 to execute the steps of the inventive method.

The ECG signal processor 4-100 also comprises circuitry for various clocks, interrupts and the like, and these are generally depicted by reference numeral 4-130. The ECG signal processor 4-100 further comprises a storage interface 4-145 to a storage system 4-190. When the ECG signal processor 4-100 is switched off, the storage system 4-190 may store the software that implements the processing functions, and on power-up, the software is read into semiconductor memory 4-150. The storage system 4-190 also retains operating and variables over power-off periods. The various elements 4-110 through 4-150 intercommunicate via a bus 4-105, which carries address signals, data signals and control signals, as is well known to those skilled in the art.

For inputting ECG signals to be analyzed, the ECG signal processor 4-100 comprises an ECG interface 4-135. An external or internal add-on to a conventional ECG apparatus typically obtains the ECG signals (or a subset of the signals) from the ECG apparatus. A stand-alone ECG signal processor must naturally duplicate the hardware and software of ECG signal reception normally implemented in an ECG apparatus.

Materials and Methods

The study population consisted of 20 apparently healthy men who came to donate blood at the Red Cross office in Kuopio, Finland, and gave their consent to participate in the present study.

Exclusion criteria included a diagnosed cardiovascular disease, a complete left- or right bundle branch block, atrial flimmer or flutter or another symptomatic arrhythmia. Four men were excluded from the final study population after the recruiting. Three men were excluded because they had forgotten to tell that they took medication for hypertension. One man was excluded before amplitude measurements because of suspected disconnection of ECG leads.

The final study population consisted of 16 men aged 19 to 63 years (47.4+/−13.3 years). The experimental protocol was approved by the University Hospital of Kuopio Clinical Investigation Committee. A written consent was obtained of all participants.

Electrocardiography

Twelve-lead ECG was recorded before and after the blood donation using Siemens Megacart Electrocardiograph (Siemens-Elema A B, Sweden). Disposable ECG electrodes (AMBU blue sensor, SU-OO-A, Malaysia) and standard electrode placement procedure (16) were used. For locating the electrode V4 "half point" procedure (16) was used. For locating the midsternal and midaxillary lines, a spirit level was used in a standing position. A one millivolt calibration signal was recorded on every channel. Paper speed of 50 mm/sec was used. The subjects were instructed to breathe quietly during the recording.

All ECG recordings were made by the inventor. ECG was registered in a supine position on an ECG recording bed. After the recording, only the cables were removed and the electrodes remained in situ. The subjects walked into another room to donate about 500 ml blood, and the second ECG was recorded after the donation on the same bed as the first ECG. No food, drink or tobacco was allowed between the blood donation and the second ECG recording.

The amplitude measurements were performed manually by the inventor with the aid of four and half fold magnification. The voltage measurements were made to the nearest 0.05 mV. R, S and T wave amplitudes were measured as a mean of three consecutive waves. QRS amplitudes were measured as the vertical distance from the PR segment to the peak of the R wave or the maximal dip of the S wave. T wave amplitude was measured from the PR segment to the peak of the T wave or to the maximal dip of a negative T wave. The electrical axis of the R and T wave was determined of the leads I and III (20).

In addition to the amplitude measurements of the single leads, some amplitude sums were also calculated. They were SV1+RV5 or V6, Sokolow-Lyon (17), RaVL+SV3, Cornell voltage criteria (18), R I+SIII, Gubner-Ungerleider (19), QRS sum, QRS sum of chest leads and QRS sum of limb leads. The QRS sum was measured from the maximum positive deflection of the R wave to the maximum negative deflection of the Q or S wave.

To find out the possible effect of variations in autonomic tone on the changes in T wave amplitudes also QT interval (QT) and corrected QT interval (QTc) were measured. The tangent method (21) was used in the measurement of QT. QTc was measured with Bazett's correction formula (22).

Statistical Analysis

All data are expressed as mean+/− standard deviation (SD). Students paired, two tailed t-test was used for the comparison between the mean amplitude values before and after the blood donation. A p value<0.05 was considered statistically significant. The t-distribution was used to calculate 95% confidence intervals (CI). The coefficient of variation (CV) was calculated as 1 SD of the difference between paired voltage measurements divided by the average mean value. It was quoted as percentage.

Results

Figure 5:
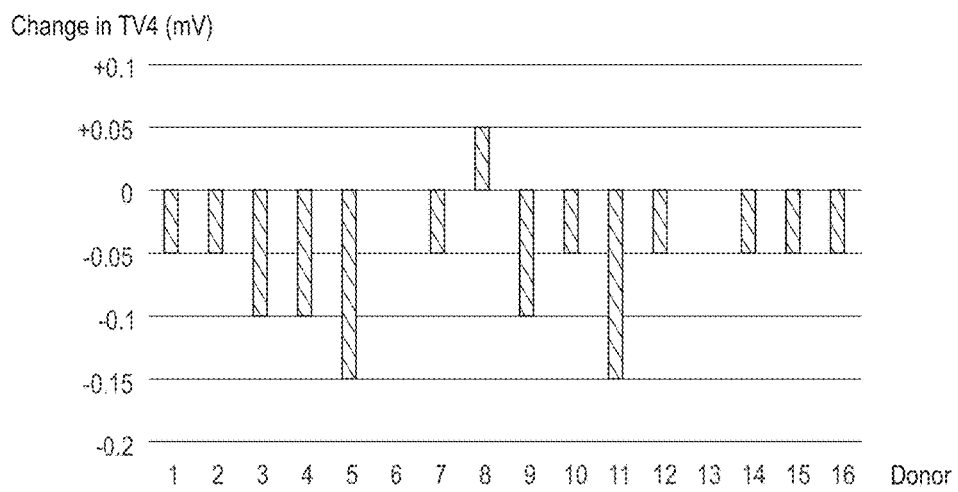
FIG. 5 shows changes in TV4 amplitude after blood donation in 16 donors.

Table 1 indicates T wave amplitudes of the chest leads. In all chest leads, except lead V1, T wave amplitude exhibited a statistically significant decrease, with p<0.05 in lead V2, p<0.01 in leads V3 and V6 and p<0.001 in leads V4 and V5. In lead V4, T wave amplitude decreased in 13 donors, did not change in two donors and increased from 0.65 mV to 0.7 mV in one donor. The changes of TV4 amplitude after blood donation in 16 donors are shown in FIG. 5. CI was 0.03 mV to 0.11 mV (4.7% to 17.2%) in lead V3, 0.03 mV to 0.09 mV (6.4% to 19.1%) in lead V4 and 0.02mV to 0.7mV (5.7% to 20.0%) in lead V5. CV in leads V2 to V6 was 11.7 to 12.3. T wave amplitude was greatest before and after the blood donation in lead V2, imaging a stable T wave axis on the horizontal plane.

Figure 6:
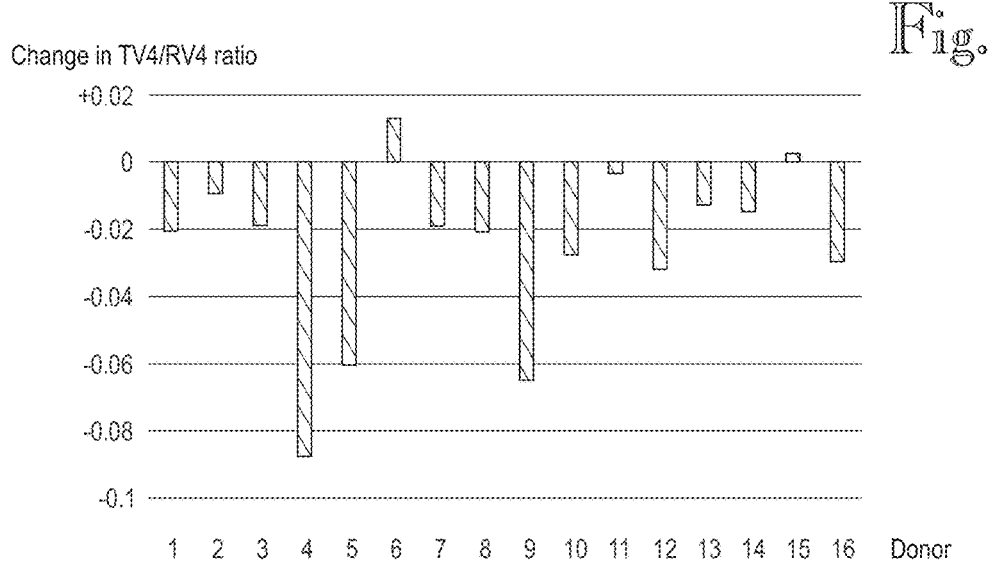
FIG. 6 shows changes in the TV4/RV4 amplitude ratio after blood donation.

T/R amplitude ratio decreased significantly in leads V4 (p<0.01) and V5 (p<0.05). Also in leads V2, V3 and V6 T/R amplitude ratio decreased, but not significantly. CI of T/R amplitude ratio was 0.0118 to 0.0395 (4.8% to 16.0%) in lead V4 and 0.0071 to 0.0421 (3.0% to 17.9%) in lead V5. The changes of TV4/RV4 amplitude ratio are shown in FIG. 6.

Table 2 shows that in limb leads, all mean positive T waves decreased after blood donation. The change was, however, significant only in lead II. The difference between mean T wave amplitudes before and after blood donation was small, and CI was 0.01 to 0.03. There was only a small and insignificant change in T wave axis (34.9 before and 35.8 after the donation).

Table 3 indicates R wave amplitudes of chest leads. A statistically significant (p<0.05) decrease was found in the mean amplitudes of RV1, RV2 and RV3. The differences between the mean amplitudes before and after blood donation were, however, small and the lower limit CI was 0 to 0.01. Also the mean amplitudes of RV4, RV5 and RV6 were greater before than after the donation, but the differences were not statistically significant. The highest mean R wave amplitude was in lead V4 before and after the donation imaging a stable electrical axis on the horizontal plane.

Table 4 indicates R wave amplitudes and the electrical axis of limb leads before and after blood donation. The mean R wave amplitude was greater before the donation than after it in four leads. The differences were not statistically significant. In leads aVR and aVL there was no difference in the mean R wave amplitude before and after the donation. The electrical axis was 45.1 before and 43.3 after the donation. The difference was not statistically significant.

CV of the change of mean R wave amplitude was 6.1 to 20.8 (mean 12) in limb leads and 5.1 to 9.7 (mean 7.9) in chest leads.

Table 5 indicates some voltage sums before and after blood donation. Most of the voltage sums decreased. The sum RI+SIII remained same and the sum RaVL+SV3 increased from 1.48 mV to 1.50 mV. All changes were insignificant. The CV of the changes was between 3.8 and 10.4, with a mean value of 6.4. There was no statistical difference in mean QT or QTc before and after blood donation.

Table 6 indicates TVn/RVn ratios for n=1 through 6, before (B) and after (A) blood donation.

All examinees were symptomless after the blood donation. There were no pathological findings in the ECGs of the donors before or after the blood donation. In two donors, one ventricular extrasystole was seen after the donation. The weight of the blood donors was 68 to 105 kg (83.25+/−10.5 kg), and body mass index (MBI) 21.3 to 31.9 (26.0+/−2.9). The length of the blood withdrawal time was usually about six minutes and at most 12 min. The time difference between the ECG registrations before and after the donation was 17 to 28 min. (21.8+/−2.7 min). Heart rate before the donation was 46 to 81 minutes (62.1+/−10.8) and 48 to 79 minutes (60.5+/−8.3) after the donation. The difference was statistically not significant.

Discussion

In chest leads all mean T wave amplitudes decreased after blood donation. The decrease was significant in all leads except lead V1. The smallest p-values were found in leads V4 and V5 (<0.001). T/R amplitude ratio decreased also significantly in leads V4 (p<0.01) and V5 (p<0.05). Because QT and QTc did not change, it is unlikely that variations in autonomic tone changed T wave amplitudes significantly.

T wave decreases, especially in anterolateral chest leads, were more pronounced than R wave decreases. This finding is in accordance with the findings of Feldman et al (15). They used Valsalva maneuver to decrease left ventricular end-diastolic dimension. In their study T wave amplitude and T/R amplitude ratio decreased significantly in leads V5 and V6 (p<0.01). The investigators also measured endocardial and epicardial surface areas with the aid of echocardiogram. They noticed that the endocardial area changed more than the epicardial area did. The increase in the ratio of endocardial/epicardial surface area of the smallest to largest was 23%. According to the investigators this augmented effect of endocardium in T wave amplitudes was the possible reason for the T wave changes.

In all limb leads the mean amplitude of positive T waves decreased after the donation in the present study. The differences were, however, small and significant only in lead II (p<0.05). In the study of Feldman et al (15) the T wave amplitude decreased significantly in leads I (p<0.05), II (p<0.01) and III (p<0.05). However, in the present study about 8% of the blood volume was removed, and it can be estimated, that because the mean heart rate did not change, the stroke volume and so the left ventricular end-diastolic volume decreased also about 8%. On the other hand, in the study of Feldman et al (15) the end-diastolic diameter decreased about 10%, and after the formula of the volume of an ellipsoid, the end-diastolic volume decreased about 30%.

Although statistically significant (p<0.05) decreases were found in the present study in R wave amplitudes only in leads V1 to V3, decreased most mean R wave amplitudes and amplitude sums after blood donation. There was no change in the mean amplitudes of RIII, RaVR and RaVL and of the amplitude sum of RI+SIII. The mean amplitude sum RaVL+SV3 increased from 1.48 mV to 1.50 mV. An explanation for the insignificant R wave and amplitude sum decreases can be the relatively low decrease of the left ventricular volume.

In animal experiments QRS amplitude decreases have been found after withdrawal of blood. Plisek and Utrata (4) removed blood from six rabbits. After blood loss of 2% of the weight of animals a decrease in the R wave amplitude of the leads I, II, III and V1-V3 was noticed. Manoch et al (5) found R wave decreases in six cats after blood loss of 16-26 ml/weight kg in the leads I, II and III. Della Torre et al (6) studied mean 27 kg weighing dogs. After removal of 460 ml blood decreased QRS amplitude in lead II 14% from the maximum positive deflection of the R wave to the maximum negative deflection on the Q or S wave. The decrease in lead aVL was even greater. In all these examinations the relative blood loss was greater than in the present one.

In human experiments indirect methods have been used to modify central blood volume, and the results have been conflicting.

In some studies QRS amplitudes have decreased with decreasing central blood volume. Castini et al (7) placed simultaneously inflating sphygmomanometric cuffs around the most proximal portions of each of the four limbs. Five minutes after the cuff inflation echocardiograms were recorded with vectorcardiographic loops and scalar Frank leads. The end-diastolic left ventricular diameter decreased 7.4% (p<0.001), Ry 8.0% (p<0.05), Rx+Ry+Rz 4.7% (p<0.05) and maximal vector in horizontal plane 5.6% (p<0.01) and in frontal plane 5.7% (p<0.01).

Feldman et al (8) investigated the effect of Valsalva maneuver and methoxamine infusion in 15 healthy man. Left ventricular dimension increased with methoxamine and decreased with Valsalva maneuver (p<0.001). R wave amplitudes in leads V5 and V6 varied directly with left ventricular dimensions (p<0.001). No significant changes were seen in leads I, II, III, aVL, aVF and V1.

In the study of Hoberg et al (9) decreased left ventricular diameter after inhalation of isoamyl nitrite 7.7% and RV5 amplitude 15% below control. After Valsalva maneuver the values were 8.6% and 12.9%, respectively.

In the above mentioned studies decreased left ventricular volume about 20% to 30% estimated of the decrease of the end-diastolic diameter. This decrease of left ventricular volume was distinctly more than the estimated 8% decrease in the present study.

In some other human studies QRS amplitudes increased when central blood volume decreased. Ishikawa et al (11) investigated effects of sauna bathing. Left ventricular internal dimension decreased from 47.2 mm to 44.9 mm (p<0.001). On the other hand S wave amplitude in Frank lead x increased from 0.18 mV to 0.24 mV (p<0.001), Q wave amplitude in lead z from 0.44 to 0.47 mV (p<0.005) and R wave amplitude in lead z from 0.74 to 0.78 mV (p<0.05).

Ishikawa et al (12) injected 50 to 60 ml amidotrizoate sodium meglumine intravenously through the right cubital vein in 25 to 30 sec to ten healthy men. Two minutes after injection Rx amplitude of Frank leads decreased from 1.18 to 1.09 mV (p<0.01), Ry amplitude from 1.06 to 0.99 mV (p<0.05), Qz amplitude from 0.44 to 0.42 mV (p<0.01) and the maximal spatial voltage from 1.57 mV to 1.48 mV (p<0.01). On the other hand, the left ventricular end-diastolic dimension increased from 47.4 to 50.4 mm (p<0.01).

Vancheri et Barberi (13) infused frusemide to 14 healthy subjects. Left ventricular end-diastolic diameter decreased from 4.69 cm to 4.39 cm (p<0.001), whereas the sum of QRS amplitude increased from 54.6 mV to 59.6 mV (p<0.001).

Mc Manus et al (14) used progressive lower body negative pressure to induce central hypovolemia in 13 healthy men. In their study R wave amplitude in lead II increased (p<0.0001) linearly with progressive lower body negative pressure. The amalgamated correlation (R2) between average stroke volume and average R wave amplitude at each lower body negative pressure stage was −0.9899.

In the opinion of the inventor, however, an alternative explanation for those opposite findings can be found. In one investigation (11) dehydration and in another (13) infusion of frusemide have probable caused decrease of extracellular fluid and increase in tissue resistance. After the law of Ohm this increase in resistance augments surface ECG potentials (23). An opposite phenomenon is possible in the study of Ishikawa et al (12), where injection of Urografin have perhaps increased extracellular fluid and decreased tissue resistance and surface potentials (23). In the study of McManus et al (14) the lower body negative pressure has possible changed the position of the heart and in that way caused the amplitude changes. Also the decrease of central blood volume was >500 ml.

It can be hypothesized, that when other circumstances remain stable, acute blood loss decreases both T wave and QRS amplitudes. The change is greatest in T wave amplitude and T/R amplitude ratio of anterolateral chest leads and happens already after a blood loss of 500 ml. A statistically significant change in T wave amplitudes of limb leads and R wave amplitudes needs perhaps a greater blood loss.

In the opinion of the inventor, the present results appear to support the theory of Brody (1), and conflicting opinions can be attributed to other factors, such as suboptimal test arrangements.

For instance, reliance on QRS amplitude measurement from chest leads has been criticized because of great variations in serial measurements (16). In the research work leading to the present invention, where a standardized procedure was used for electrode placements, and the electrodes were not removed between the registrations, there was no practical difference between the coefficients of variation of R wave amplitude of the limb and chest leads (mean values 12 and 7.9, respectively).

Farb et al (24), Van Den Hoogen and al (25) and McLaughlin et al (26) have studied the day-to-day and minute-to-minute variation of ECG amplitudes used for left ventricular hypertrophy. In day-to-day series the tracings were made without marking the previous electrode placement. In minute-to-minute series the electrodes were not removed between the tracings.

The coefficients of variation in the present study were between the day-to-day and minute-to-minute values published in reference documents (24) through (26). One plausible explanation is that the electrodes have moved a little, when the donors walked to another room and back, and this movement has caused the higher values compared with the minute-to-minute series.

Angeli et al. (27) compared the day-to-day variation of QRS amplitudes in a group of 142 patients with the position of the electrodes marked on the skin and 134 traditional ECG without marking the positions of electrodes. The coefficient of variation in the traditional group was from 30 to 64 in limb leads and from 45 to 81 in the chest leads. In the group with marked electrode positions, the variations were from 26 to 66 in the limb leads and from 34 to 47 in the chest leads. The corresponding values for the Sokolow-Lyon voltage were 20 and 14, and for the Cornell voltage the values were 22 and 17. These coefficients of variation are much higher than the coefficients in the present study. Angeli et al. emphasize the fact that their study was a multicenter study and the ECG procedures were not standardized. These findings show the importance to use standardized procedures when ECG amplitudes are compared in serial registrations.

Van Den Hoogen et al (25) measured the coefficients of variation also for some T wave amplitudes. The day-to-day and minute-to-minute variations were 37.5 and 16.5 in T I, 31.1 and 14.0 in T II, 42.2 and 17.8 in T V1 and 22.0 and 6.7 in T V2. The coefficients of variation of the amplitudes of T waves of the same leads in the present study were 15.7 in T1. 7.5 in T II, 20.5 in V1 and 11.7 in V2, that was not much different from the minute-to-minute values of Van Den Hoogen et al.

In the light of the above mentioned results it seems that the coefficients of variation obtained by the inventor are not too high to exclude meaningful comparisons between the QRS and T wave amplitudes in serial measurements.

Limitations of the Present Study

The material in the present study was small. However, the purpose was primarily to find out if any consistent changes in QRS and T wave amplitudes and T/R amplitude ratios could be found in men after a blood donation of 500 ml. It was also estimated that if a greater number of donors was necessary to obtain statistically significant changes in amplitude, the practical significance would be negligible. Also in most of the previous studies there were only 10 to 15 subjects.

Despite the fact that QT and QTc did not change, the possible effect of changes in autonomic tone in the changes in T wave amplitudes can be completely excluded. The possible effect is, however, estimated negligible.

The recordings were made in the office of the local Red Cross. This office was planned only for blood donation. Therefore the equipment for the study was kept as simple as possible. Only an electrocardiograph without automatic data processing was used. Also because of limited space, only men were investigated. In women the difference in breast protuberance among different individuals explains less than 1% of ECG amplitude variations (16). So, breast tuberance has no practical effect on ECG amplitudes, and the same standardized electrode placement can be used for men and women alike.

The errors introduced by beat-to-beat variation are not entirely eliminated, when the measurements are made from three beats only. Without automatic recording, however, measurements from a greater number of beats would have been too cumbersome in comparison with the practical benefit.

Also the manual voltage measurements to the nearest 0.05 mV may have caused quantification errors. However, manual and automated measurements of the sums of the amplitudes of the QRS complexes and T waves are well correlated and differ by approximately 9%, with manual measurements generating lower values (28).

Quiet resting respiration during recording may cause variations in the amplitudes. However, the effect of respiration is small on the average (29).

The diameter of the left ventricle was not measured in the present study. However, because the blood volume decreased about 8%, it is probable, that also venous return decreased about 8%. Because heart rate did not change, it can be estimated that stroke volume and left ventricular end-diastolic volume decreased about 8%.

Arterial pressure was not measured. However, blood loss in donation is about 500 ml, and about 10% of the total blood volume can be removed with almost no effect on either arterial pressure or cardiac output (30).

Conclusion

Supporting the theory of Brody, T wave amplitudes and T/R amplitude ratios of anterolateral chest leads decreased statistically significantly (p<0.001 and p<0.01) in healthy men after blood donation of 500 ml. The changes were greatest in lead V4. Also positive T waves in limb leads and most R waves in limb and chest leads decreased after blood donation. Most of these decreases were, however, insignificant.

In view of the present investigation, T wave amplitude and T/R amplitude ratio decrease in anterolateral chest leads, especially in lead V4, may be a sign of symptomless blood loss in men. In the care of a patient with these findings attention must be paid to the possibility of the risk of a significant acute hemorrhage.

The present invention is based on blood volume determination. In the present invention, the relative blood volume of a postoperative patient is compared with the blood volume of the patient at the start of the postoperative monitoring. Blood volume is estimated by comparing the TV4 wave amplitude of ECG with the TV4 amplitude at the start of the monitoring. The T amplitude used in the present invention is dependent on blood volume. The method and apparatus of the present invention are intended to monitor, whether early postoperative blood volume of the patient is on a level that causes no harm for the patient (more than 90 percent of the normal blood volume), using ECG amplitude measurements that are specific for blood volume.

Human blood volume may decrease 10% without harm. For example, blood donation removes 500 ml of blood without health consequences. Also, the patient's blood pressure or pulse density does not usually change.

The present invention provides a noninvasive and simple method for demonstrating a low decrease of blood volume. The purpose of the proposed method and device is to facilitate postoperative monitoring of patients by monitoring the amount of blood volume even with a minor (0-10%) reduction.

In practice, the monitoring is performed by monitoring the magnitude of the repolarization amplitude (T wave) measured by the unipolar electrode corresponding to ECG coupling V4. The position of the electrode is determined by standardized measurement, rather than visually, as is usually the case. This electrode acts as a positive electrode and acts as a negative electrode with electrodes of both wrists and left ankle coupled with 5000 ohm resistors as in the normal ECG breast plugs. The device indicates the measured voltage percentages as compared to the voltage measured at the beginning of postoperative monitoring, marked by 100%.

Based on experimental results, the change in voltage (amplitude) of 7 microvolts (μV) is about 1% change in human blood volume. As a result of the amplitude reduction of 70 μV, the blood volume is thus 90% and 35 μV respectively decreases 95%. The percentage of continuous percentages is shown on the display of the device. If the percentage reading is greater than 90, the blood volume is large enough. If the blood volume drops to 90%, there is usually no need for the patient to do so, but the practitioner may, at his discretion, consult a physician responsible for the department. The device alerts every 5% of the blood volume after a fall.

The postoperative follow-up manager must almost always monitor several patients, and the present method may exclude some of the studies performed by the nurse (e.g. numerous blood pressure measurements), leaving the nurse more time to monitor patients.

The present invention discloses an ECG device that has the additional capacity to monitor blood volume.

Partly through the use of shared technology, cost savings are achieved. Also, the manufacturing of the device is unlikely to be significantly more expensive than that of a conventional ECG device. The same device may be used for everything that the ECG device does, but the additional feature is the blood volume monitoring.

Those skilled in the art will realize that the inventive principle may be modified in various ways without departing from the scope of the attached claims.

Tables

TABLE 1

T wave amplitudes (mV) of chest leads before (B) and after (A) blood donation

| Donor | TV1 B | TV1 A | TV2 B | TV2 A | TV3 B | TV3 A | TV4 B | TV4 A | TV5 B | TV5 A | TV6 B | TV6 A |
|---|---|---|---|---|---|---|---|---|---|---|---|---|
| 1 | 0.2 | 0.15 | 0.8 | 0.8 | 0.7 | 0.65 | 0.55 | 0.5 | 0.5 | 0.45 | 0.35 | 0.35 |
| 2 | −0.05 | −0.05 | 1 | 1 | 1.2 | 1.2 | 1.1 | 1.05 | 0.85 | 0.8 | 0.5 | 0.5 |
| 3 | 0.15 | 0.1 | 1.1 | 1.05 | 1.1 | 1 | 0.85 | 0.75 | 0.5 | 0.4 | 0.35 | 0.3 |
| 4 | 0.15 | 0.15 | 0.6 | 0.55 | 0.55 | 0.55 | 0.4 | 0.3 | 0.25 | 0.2 | 0.2 | 0.15 |
| 5 | 0.45 | 0.4 | 0.75 | 0.6 | 0.6 | 0.35 | 0.3 | 0.15 | 0.2 | 0.15 | 0.15 | 0.15 |
| 6 | 0.15 | 0.15 | 0.55 | 0.55 | 0.3 | 0.3 | 0.15 | 0.15 | 0.15 | 0.15 | 0.15 | 0.15 |
| 7 | 0 | 0 | 0.8 | 0.7 | 1.1 | 0.95 | 0.75 | 0.7 | 0.5 | 0.5 | 0.35 | 0.35 |
| 8 | 0.25 | 0.25 | 0.8 | 0.95 | 0.85 | 0.9 | 0.65 | 0.7 | 0.45 | 0.5 | 0.35 | 0.35 |
| 9 | 0.15 | 0.15 | 0.75 | 0.65 | 0.7 | 0.6 | 0.5 | 0.4 | 0.3 | 0.2 | 0.2 | 0.15 |
| 10 | 0.15 | 0.15 | 0.5 | 0.45 | 0.35 | 0.3 | 0.1 | 0.05 | 0.05 | 0 | 0.1 | 0.1 |
| 11 | 0.2 | 0.15 | 0.7 | 0.5 | 0.5 | 0.35 | 0.45 | 0.3 | 0.35 | 0.25 | 0.3 | 0.2 |
| 12 | 0.15 | 0.2 | 0.7 | 0.7 | 0.55 | 0.5 | 0.4 | 0.35 | 0.3 | 0.3 | 0.25 | 0.2 |
| 13 | 0.1 | 0.1 | 0.6 | 0.55 | 0.5 | 0.5 | 0.35 | 0.35 | 0.3 | 0.25 | 0.2 | 0.2 |
| 14 | 0.1 | 0.1 | 0.65 | 0.55 | 0.55 | 0.45 | 0.4 | 0.35 | 0.35 | 0.3 | 0.3 | 0.25 |
| 15 | −0.1 | −0.1 | 0.3 | 0.2 | 0.35 | 0.25 | 0.3 | 0.25 | 0.25 | 0.2 | 0.25 | 0.2 |
| 16 | 0.3 | 0.25 | 0.6 | 0.55 | 0.5 | 0.5 | 0.3 | 0.25 | 0.35 | 0.3 | 0.3 | 0.3 |
| Mean | 0.15 | 0.13 | 0.7 | 0.65 | 0.64 | 0.57 | 0.47 | 0.41 | 0.35 | 0.31 | 0.27 | 0.24 |
| SD | 0.13 | 0.12 | 0.19 | 0.22 | 0.29 | 0.29 | 0.26 | 0.26 | 0.18 | 0.19 | 0.1 | 0.11 |
| P | NS | | <0.05 | | <0.01 | | <0.001 | | <0.001 | | <0.01 | |
| CI | | | 0.01-0.03 | | 0.03-0.11 | | 0.03-0.09 | | 0.02-0.07 | | 0.01-0.04 | |
| CV | 20.5 | | 11.7 | | 12.5 | | 11.8 | | 12.2 | | 12.3 | |

NS = not significant,
CI = confidence interval,
CV = coefficient of variation

TABLE 2

T wave amplitudes (mV) and T wave axis (degrees) of limb leads before (B) and after (A) blood donation

| Donor | TI B | TI A | TII B | TII A | TIII B | TIII A | TaVR B | TaVR A | TaVL B | TaVL A | TaVF B | TaVF A | T wave axis B | T wave axis A |
|---|---|---|---|---|---|---|---|---|---|---|---|---|---|---|
| 1 | 0.3 | 0.3 | 0.4 | 0.4 | 0.1 | 0.1 | −0.4 | −0.35 | 0.1 | 0.15 | 0.25 | 0.25 | 44 | 44 |
| 2 | 0.5 | 0.5 | 0.6 | 0.55 | 0.15 | 0.05 | −0.5 | −0.5 | 0.15 | 0.2 | 0.35 | 0.3 | 43 | 35 |

TABLE 2-continued

T wave amplitudes (mV) and T wave axis (degrees) of
limb leads before (B) and after (A) blood donation

|  | TI | | TII | | TIII | | TaVR | | TaVL | | TaVF | | T wave axis | |
|---|---|---|---|---|---|---|---|---|---|---|---|---|---|---|
| Donor | B | A | B | A | B | A | B | A | B | A | B | A | B | A |
| 3 | 0.3 | 0.3 | 0.35 | 0.35 | −0.05 | 0.1 | −0.35 | −0.3 | 0.2 | 0.1 | 0.2 | 0.2 | 21 | 44 |
| 4 | 0.2 | 0.2 | 0.25 | 0.25 | 0.1 | 0.05 | −0.2 | −0.2 | 0.05 | 0.05 | 0.2 | 0.15 | 49 | 41 |
| 5 | 0.1 | 0.15 | 0.25 | 0.2 | 0.1 | 0.1 | −0.2 | −0.15 | 0.05 | 0 | 0.15 | 0.2 | 60 | 53 |
| 6 | 0.1 | 0.1 | 0.15 | 0.15 | 0 | 0.05 | −0.1 | −0.1 | 0.05 | 0 | 0.1 | 0.1 | 30 | 44 |
| 7 | 0.45 | 0.45 | 0.3 | 0.25 | −0.2 | −0.2 | −0.4 | −0.4 | 0.3 | 0.3 | 0.15 | 0.1 | 4 | 4 |
| 8 | 0.2 | 0.25 | 0.5 | 0.55 | 0.3 | 0.25 | −0.35 | −0.4 | 0.05 | 0 | 0.4 | 0.4 | 66 | 60 |
| 9 | 0.25 | 0.2 | 0.2 | 0.15 | −0.05 | −0.05 | −0.2 | −0.2 | 0.1 | 0.15 | 0.1 | 0.1 | 18 | 15 |
| 10 | 0.15 | 0.1 | 0 | 0 | −0.05 | 0 | −0.1 | −0.1 | 0.1 | 0 | 0 | 0 | 10 | 30 |
| 11 | 0.4 | 0.35 | 0.3 | 0.25 | −0.1 | −0.1 | −0.35 | −0.3 | 0.25 | 0.2 | 0.1 | 0.1 | 16 | 13 |
| 12 | 0.25 | 0.2 | 0.3 | 0.25 | 0.1 | 0.05 | −0.25 | −0.25 | 0.1 | 0.1 | 0.2 | 0.15 | 46 | 41 |
| 13 | 0.3 | 0.25 | 0.25 | 0.2 | −0.05 | −0.1 | −0.3 | −0.25 | 0.15 | 0.2 | 0.1 | 0.1 | 21 | 6 |
| 14 | 0.3 | 0.3 | 0.3 | 0.3 | 0 | 0 | −0.3 | −0.3 | 0.15 | 0.15 | 0.15 | 0.15 | 30 | 30 |
| 15 | 0.2 | 0.15 | 0.3 | 0.3 | 0.1 | 0.1 | −0.25 | −0.2 | 0.1 | 0 | 0.2 | 0.2 | 49 | 53 |
| 16 | 0.25 | 0.15 | 0.4 | 0.35 | 0.15 | 0.15 | −0.3 | −0.25 | 0.05 | 0 | 0.25 | 0.25 | 52 | 60 |
| Mean | 0.27 | 0.25 | 0.3 | 0.28 | 0.04 | 0.03 | −0.28 | −0.27 | 0.12 | 0.1 | 0.18 | 0.17 | 34.94 | 35.81 |
| SD | 0.11 | 0.12 | 0.14 | 0.14 | 0.18 | 0.11 | 0.11 | 0.11 | 0.08 | 0.1 | 0.1 | 0.1 | 18.64 | 18.14 |
| P | NS | | <0.05 | | NS | | <0.05 | | NS | | NS | | NS | |
| CI | | | 0.01-0.03 | | | | −0.04-0 | | | | | | | |
| CV | 15.7 | | 7.5 | | | | | | 49.3 | | 15.4 | | | |

NS = not significant,
CI = confidence interval,
CV = coefficient of variation

TABLE 3

R wave amplitudes (mV) of chest leads before (B) and after (A) blood donation

|  | RV1 | | RV2 | | RV3 | | RV4 | | RV5 | | RV6 | |
|---|---|---|---|---|---|---|---|---|---|---|---|---|
| Donor | B | A | B | A | B | A | B | A | B | A | B | A |
| 1 | 0.6 | 0.6 | 1.2 | 1.25 | 1.5 | 1.5 | 1.6 | 1.55 | 1.15 | 1.15 | 0.8 | 0.75 |
| 2 | 0.3 | 0.3 | 1.1 | 1.05 | 1.85 | 1.8 | 3.55 | 3.5 | 2.3 | 2.25 | 1.35 | 1.3 |
| 3 | 0.4 | 0.4 | 1.45 | 1.5 | 1.35 | 1.25 | 3.4 | 3.25 | 2.6 | 2.55 | 1.9 | 1.85 |
| 4 | 0.25 | 0.25 | 0.6 | 0.6 | 0.8 | 0.8 | 0.95 | 0.9 | 1.1 | 1.05 | 0.95 | 0.9 |
| 5 | 0.6 | 0.55 | 1.25 | 1.25 | 2 | 2.1 | 2.5 | 2.55 | 1.65 | 1.7 | 1.1 | 1.15 |
| 6 | 0.1 | 0.1 | 0.7 | 0.65 | 1.25 | 1.2 | 1.15 | 1.05 | 0.85 | 0.8 | 0.75 | 0.65 |
| 7 | 0.3 | 0.3 | 1.25 | 1.25 | 1.8 | 1.8 | 2.7 | 2.7 | 2.1 | 2.15 | 1.45 | 1.5 |
| 8 | 0.4 | 0.4 | 0.95 | 0.9 | 2.05 | 1.75 | 2 | 2.3 | 1.85 | 1.7 | 1.4 | 1.3 |
| 9 | 0.3 | 0.3 | 0.6 | 0.6 | 0.65 | 0.65 | 1.7 | 1.75 | 1.8 | 1.85 | 1.45 | 1.45 |
| 10 | 0.25 | 0.25 | 0.6 | 0.55 | 0.95 | 0.85 | 1.55 | 1.35 | 1.55 | 1.4 | 1.2 | 1 |
| 11 | 0.35 | 0.3 | 0.85 | 0.75 | 1.25 | 0.85 | 1.55 | 1.05 | 1.1 | 0.8 | 0.8 | 0.65 |
| 12 | 0.3 | 0.25 | 1.05 | 1.05 | 1.25 | 1.25 | 1.55 | 1.55 | 1.35 | 1.3 | 1 | 0.95 |
| 13 | 0.1 | 0.1 | 0.2 | 0.2 | 0.8 | 0.7 | 1.6 | 1.7 | 1.1 | 1.3 | 1.1 | 1.3 |
| 14 | 0.4 | 0.35 | 0.9 | 0.8 | 1.2 | 1.1 | 1.2 | 1.1 | 1 | 1 | 0.8 | 0.8 |
| 15 | 0.3 | 0.3 | 0.7 | 0.65 | 1.05 | 0.95 | 1.95 | 1.6 | 1.5 | 1.25 | 0.9 | 0.8 |
| 16 | 0.25 | 0.25 | 0.9 | 0.85 | 1.8 | 1.75 | 1.9 | 1.95 | 1.5 | 1.55 | 1.25 | 1.25 |
| Mean | 0.33 | 0.31 | 0.89 | 0.87 | 1.35 | 1.27 | 1.93 | 1.87 | 1.53 | 1.49 | 1.14 | 1.1 |
| SD | 0.14 | 0.13 | 0.32 | 0.34 | 0.45 | 0.46 | 0.75 | 0.79 | 0.5 | 0.52 | 0.32 | 0.34 |
| P | <0.05 | | <0.05 | | <0.05 | | NS | | NS | | NS | |
| CI | 0-0.02 | | 0-0.05 | | 0.01-0.14 | | | | | | | |
| CV | 7 | | 5.1 | | 9.3 | | 9.7 | | 8.2 | | 8.2 | |

NS = not significant,
CI = confidence interval,
CV = coefficient of variation

TABLE 4

R wave amplitudes (mV) and T wave axis (degrees) of limb leads before (B) and after (A) blood donation

|  | RI | | RII | | RIII | | aVR | | aVL | | aVF | | Electrical axis | |
|---|---|---|---|---|---|---|---|---|---|---|---|---|---|---|
| Donor | B | A | B | A | B | A | B | A | B | A | B | A | B | A |
| 1 | 0.7 | 0.65 | 0.7 | 0.65 | 0.2 | 0.1 | 0.2 | 0.2 | 0.3 | 0.35 | 0.4 | 0.35 | 19 | −3 |
| 2 | 0.6 | 0.7 | 1.1 | 1.05 | 0.7 | 0.6 | 0.2 | 0.2 | 0.3 | 0.35 | 0.85 | 0.8 | 68 | 61 |
| 3 | 0.6 | 0.4 | 1.95 | 2 | 1.45 | 1.65 | 0.1 | 0.1 | 0.2 | 0.1 | 1.65 | 1.75 | 72 | 81 |
| 4 | 0.95 | 1.05 | 0.7 | 0.7 | 0.1 | 0.1 | 0.1 | 0.1 | 0.6 | 0.7 | 0.2 | 0.15 | 5 | 12 |

TABLE 4-continued

R wave amplitudes (mV) and T wave axis (degrees) of limb leads before (B) and after (A) blood donation

| Donor | RI B | RI A | RII B | RII A | RIII B | RIII A | aVR B | aVR A | aVL B | aVL A | aVF B | aVF A | Electrical axis B | Electrical axis A |
|---|---|---|---|---|---|---|---|---|---|---|---|---|---|---|
| 5 | 0.75 | 0.7 | 1.65 | 1.65 | 1.1 | 1.1 | 0 | 0 | 0.1 | 0.1 | 1.3 | 1.35 | 66 | 67 |
| 6 | 0.4 | 0.4 | 0.75 | 0.6 | 0.4 | 0.35 | 0 | 0 | 0.1 | 0.15 | 0.55 | 0.45 | 55 | 52 |
| 7 | 0.9 | 0.95 | 1.35 | 1.4 | 0.8 | 0.85 | 0.05 | 0.1 | 0.3 | 0.3 | 0.9 | 0.9 | 59 | 58 |
| 8 | 0.8 | 0.8 | 1.9 | 1.9 | 1.6 | 1.5 | 0.1 | 0.1 | 0.2 | 0.15 | 1.75 | 1.7 | 71 | 70 |
| 9 | 0.8 | 0.75 | 1.15 | 1.1 | 0.5 | 0.45 | 0.05 | 0 | 0.4 | 0.3 | 0.8 | 0.75 | 53 | 52 |
| 10 | 1.15 | 1.1 | 0.7 | 0.5 | 0.25 | 0.2 | 0.2 | 0.2 | 0.85 | 0.9 | 0.15 | 0.1 | 3 | −12 |
| 11 | 1 | 1.05 | 0.35 | 0.35 | 0.05 | 0.05 | 0.3 | 0.3 | 0.85 | 0.7 | 0.1 | 0.05 | 26 | 26 |
| 12 | 0.5 | 0.5 | 1.1 | 1.1 | 0.65 | 0.65 | 0.25 | 0.25 | 0.25 | 0.25 | 0.85 | 0.9 | 69 | 73 |
| 13 | 1 | 1.05 | 0.9 | 0.9 | 0.25 | 0.35 | 0.1 | 0.1 | 0.65 | 0.7 | 0.35 | 0.3 | 29 | 32 |
| 14 | 0.75 | 0.8 | 0.85 | 0.8 | 0.2 | 0.25 | 0.1 | 0.1 | 0.35 | 0.4 | 0.5 | 0.4 | 39 | 39 |
| 15 | 0.75 | 0.8 | 1 | 1 | 0.25 | 0.25 | 0.1 | 0.1 | 0.25 | 0.3 | 0.65 | 0.6 | 34 | 27 |
| 16 | 1 | 0.85 | 1.3 | 1.25 | 0.55 | 0.65 | 0.05 | 0 | 0.45 | 0.3 | 0.9 | 0.9 | 53 | 58 |
| Mean | 0.79 | 0.78 | 1.09 | 1.06 | 0.57 | 0.57 | 0.12 | 0.12 | 0.38 | 0.38 | 0.74 | 0.72 | 45.06 | 43.31 |
| SD | 0.2 | 0.22 | 0.45 | 0.48 | 0.47 | 0.49 | 0.09 | 0.09 | 0.24 | 0.24 | 0.49 | 0.53 | 23.37 | 27.53 |
| P | NS | | NS | | NS | | NS | | NS | | NS | | NS | |
| CV | 10.6 | | 6.1 | | 8.2 | | 18.8 | | 20.8 | | 7.5 | | | |

NS = not significant,
CV = coefficient of variation

TABLE 5

Amplitude sums of some ECG criteria for left ventricular hypertrophy before (B) and after (A) blood donation

| Donor | SV1 + RV5 B | SV1 + RV5 A | RaVL + SV3 B | RaVL + SV3 A | RI + SIII B | RI + SIII A | QRS sum B | QRS sum A | QRS Σ(chest leads) B | QRS Σ(chest leads) A | QRS Σ(limb leads) B | QRS Σ(limb leads) A |
|---|---|---|---|---|---|---|---|---|---|---|---|---|
| 1 | 2.05 | 2.05 | 2.05 | 2.15 | 1 | 1 | 16.65 | 16.9 | 12.5 | 12.65 | 4.15 | 4.25 |
| 2 | 2.8 | 2.75 | 0.65 | 0.75 | 0.65 | 0.8 | 18.75 | 18.5 | 13.25 | 13.15 | 5.4 | 5.35 |
| 3 | 3.85 | 3.75 | 2.25 | 2.2 | 0.6 | 0.4 | 27.5 | 26.8 | 19.4 | 18.85 | 8.1 | 7.95 |
| 4 | 1.9 | 1.95 | 1.6 | 1.85 | 1.45 | 1.5 | 13.9 | 14.05 | 8.9 | 9.2 | 5 | 4.85 |
| 5 | 3.1 | 3.25 | 0.6 | 0.5 | 0.75 | 0.7 | 19.05 | 18.9 | 12.55 | 12.5 | 6.5 | 6.4 |
| 6 | 1.6 | 1.55 | 0.95 | 1 | 0.4 | 0.4 | 10.9 | 10.2 | 8 | 7.7 | 2.9 | 2.5 |
| 7 | 2.65 | 2.7 | 1.35 | 1.35 | 0.9 | 0.9 | 19.05 | 19.6 | 13 | 13.25 | 6.05 | 6.35 |
| 8 | 3.1 | 2.95 | 1.9 | 1.75 | 0.8 | 0.8 | 23.85 | 22.8 | 14.95 | 14.1 | 8.9 | 8.7 |
| 9 | 3.1 | 3.15 | 2 | 1.9 | 0.4 | 0.3 | 17.65 | 17.3 | 12.65 | 12.75 | 5 | 4.55 |
| 10 | 2.4 | 2.3 | 2.25 | 2.4 | 1.85 | 1.9 | 17.3 | 17.15 | 11.5 | 11.25 | 5.8 | 5.9 |
| 11 | 1.75 | 1.5 | 2.15 | 1.9 | 1.75 | 1.8 | 15.75 | 14.1 | 10.65 | 9 | 5.1 | 5.1 |
| 12 | 2 | 1.95 | 1.45 | 1.5 | 0.8 | 0.7 | 16 | 16.8 | 10.95 | 11.1 | 5.65 | 5.7 |
| 13 | 2.65 | 2.95 | 1.55 | 1.7 | 1.25 | 1.35 | 14.3 | 15.45 | 9.35 | 10 | 4.95 | 5.45 |
| 14 | 1.85 | 1.85 | 1.3 | 1.3 | 0.8 | 0.85 | 13.45 | 13.15 | 9.65 | 9.2 | 3.8 | 3.95 |
| 15 | 2.3 | 2.05 | 0.8 | 0.9 | 0.95 | 1.1 | 14.3 | 13.6 | 9.6 | 8.8 | 4.7 | 4.8 |
| 16 | 2.5 | 2.5 | 0.9 | 0.8 | 1 | 0.85 | 16 | 15.9 | 10.25 | 10.5 | 5.75 | 5.4 |
| Mean | 2.48 | 2.45 | 1.48 | 1.5 | 0.96 | 0.96 | 17.19 | 16.95 | 11.7 | 11.5 | 5.48 | 5.45 |
| SD | 0.62 | 0.65 | 0.58 | 0.58 | 0.43 | 0.47 | 4.05 | 4 | 2.78 | 2.74 | 1.48 | 1.48 |
| P | NS | | NS | | NS | | NS | | NS | | NS | |
| CV | 5.6 | | 8.8 | | 10.4 | | 3.8 | | 4.9 | | 4.6 | |

NS = not significant,
CV = coefficient of variation

TABLE 6

TVn/RVn ratios (n = 1 ... 6) before (B) and after (A) blood donation.

| Donor | TV1/RV1 B | TV1/RV1 A | TV2/RV2 B | TV2/RV2 A | TV3/RV3 B | TV3/RV3 A | TV4/RV4 B | TV4/RV4 A | TV5/RV5 B | TV5/RV5 A | TV6/RV6 B | TV6/RV6 A |
|---|---|---|---|---|---|---|---|---|---|---|---|---|
| 1 | 0.333 | 0.25 | 0.667 | 0.64 | 0.467 | 0.433 | 0.344 | 0.323 | 0.435 | 0.391 | 0.438 | 0.467 |
| 2 | −0.167 | −0.25 | 0.909 | 0.952 | 0.647 | 0.667 | 0.31 | 0.3 | 0.37 | 0.356 | 0.37 | 0.385 |
| 3 | 0.375 | 0.25 | 0.759 | 0.7 | 0.815 | 0.8 | 0.25 | 0.231 | 0.192 | 0.157 | 0.184 | 0.162 |
| 4 | 0.6 | 0.6 | 1 | 0.917 | 0.688 | 0.688 | 0.421 | 0.333 | 0.227 | 0.19 | 0.211 | 0.167 |
| 5 | 0.75 | 0.727 | 0.6 | 0.48 | 0.3 | 0.167 | 0.12 | 0.059 | 0.121 | 0.088 | 0.136 | 0.13 |
| 6 | 1.5 | 1.5 | 0.786 | 0.846 | 0.24 | 0.25 | 0.13 | 0.143 | 0.176 | 0.188 | 0.2 | 0.231 |
| 7 | 0 | 0 | 0.64 | 0.56 | 0.611 | 0.528 | 0.278 | 0.259 | 0.238 | 0.233 | 0.241 | 0.233 |
| 8 | 0.625 | 0.625 | 0.842 | 1.056 | 0.415 | 0.514 | 0.325 | 0.304 | 0.243 | 0.294 | 0.25 | 0.269 |
| 9 | 0.5 | 0.5 | 1.25 | 1.083 | 1.077 | 0.923 | 0.294 | 0.229 | 0.167 | 0.108 | 0.138 | 0.103 |
| 10 | 0.6 | 0.6 | 0.833 | 0.818 | 0.368 | 0.353 | 0.065 | 0.037 | 0.032 | 0 | 0.083 | 0.1 |

TABLE 6-continued

TVn/RVn ratios (n = 1 ... 6) before (B) and after (A) blood donation.

| | TV1/RV1 | | TV2/RV2 | | TV3/RV3 | | TV4/RV4 | | TV5/RV5 | | TV6/RV6 | |
|---|---|---|---|---|---|---|---|---|---|---|---|---|
| Donor | B | A | B | A | B | A | B | A | B | A | B | A |
| 11 | 0.571 | 0.5 | 0.824 | 0.667 | 0.4 | 0.412 | 0.29 | 0.286 | 0.318 | 0.313 | 0.375 | 0.308 |
| 12 | 0.5 | 0.8 | 0.667 | 0.667 | 0.44 | 0.4 | 0.258 | 0.226 | 0.222 | 0.231 | 0.25 | 0.211 |
| 13 | 1 | 1 | 3 | 2.75 | 0.625 | 0.714 | 0.219 | 0.206 | 0.273 | 0.192 | 0.182 | 0.154 |
| 14 | 0.25 | 0.286 | 0.722 | 0.688 | 0.458 | 0.409 | 0.333 | 0.318 | 0.35 | 0.3 | 0.375 | 0.313 |
| 15 | −0.333 | −0.333 | 0.429 | 0.308 | 0.333 | 0.263 | 0.154 | 0.156 | 0.167 | 0.16 | 0.278 | 0.25 |
| 16 | 1.2 | 1 | 0.667 | 0.647 | 0.167 | 0.171 | 0.158 | 0.128 | 0.233 | 0.194 | 0.24 | 0.24 |
| Mean | 0.5190 | 0.5034 | 0.9122 | 0.8612 | 0.5032 | 0.4808 | 0.2468 | 0.2211 | 0.2353 | 0.2122 | 0.2469 | 0.2327 |
| SD | 0.4713 | 0.4729 | 0.5866 | 0.5438 | 0.2316 | 0.2255 | 0.0975 | 0.0933 | 0.0996 | 0.1023 | 0.0994 | 0.1009 |
| P | 0.5586 | | 0.0769 | | 0.2060 | | 0.0013 | | 0.0113 | | 0.0876 | |
| CI | | | | | | | 0.0118 | 0.0395 | 0.0071 | 0.0421 | | |
| CV | | | | | | | 11.1 | | 14.7 | | | |

CI = confidence interval,
CV = coefficient of variation

REFERENCE DOCUMENTS

1. Brody A.: *A theoretical analysis of intracavitary blood mass influence on the heart-lead relationship*. Circ Res 1956; 4: 731-738.
2. Rudy Y, Plonsey R.: *Comments on the effect of variations in the size of the heart on the magnitude of ECG potentials*. J Electrocardiol 1980; 13: 79-82.
3. Nelson C V, Troquet J.: *Magnitude and location of a dipole in a circular ring with non-insulating boundaries*. J Electrocardiol 1986; 19: 347-53.
4. Plisek V, Utrata F. *Elektrokardiographische Veränderungen nach akutem Blutverlust bei Kaninchen*. Arch Kreislaufforsch 1970; 61: 181-193.
5. Manoch M, Gitter S, Grossman E, Varon D, Gassner S. *Influence of hemorrhage on the QRS complex of the electrocardiogram*. Am Heart J 1971; 82: 55-61.
6. Della Torre P K, Zaki S, Govendir M, Church D B, Malik R. *Effect of acute hemorrhage on QRS amplitude of the lead II canine electrocardiogram electrocardiogram*. Aust Vet J 1999; 77: 298-300.
7. Castini D, Vitolo E, Ornaghi M, Gentile F. *Demonstration of the relationship between heart dimensions and QRS voltage amplitudes*. J Elecrocardiol 1966; 29: 169-73.
8. Feldman T, Borow K, Neuman A, Lang R, Childers R. *Relation of electrocardiographic R-wave amplitude to changes in left ventricular chamber size and position in normal subjects*. Am J Cardiol 1985; 55: 1168-74.
9. Hoberg E, Lemke R, Klaus D. *Verhalten der R-Amplituden-Höhe bei Änderung des linksventrikulären Volumens von Herzgesunden*. Z Kardiol 1982; 71: 544-47.
10. Amoore J N, Rudy Y. *The effect of variation of ventricular volume on the electrocardiogram. A comparison of two model simulations*. J Elecrocardiol 1988; 21: 154-60.
11. Ishikawa K, Shirato C, Yanagisawa A. *Electrocardiographic changes due to sauna bathing. Influence of acute reduction in circulating blood volume on body surface potentials with special reference to the Brody effect*. Br Heart J 1983; 50: 469-75.
12. Ishikawa K, Kanamaru S, Yotsukura M, Tsuya T, Shirato C, Yanagisawa A. *Influence of peripheral intravenous contrast injection on the QRS complex in healthy men*. Cardiovascular Research 1986; 20: 61-6.
13. Vancheri F, Barberi O. *Relationship of QRS amplitude to left ventricular dimensions after acute blood volume reduction in normal subjects*. European Heart Journal 1989; 10: 341-45.
14. McManus J, Convertino V, Cooke W, Ludvig D, Holcomb J. *R-wave amplitude in lead II of an electrocardiograph correlates with central hypovolemia in human beings*. Academic Emergency Medicine 2006; 13: 1003-10.
15. Feldman T, Childers R W, Borow K M, Lang R M, Neuman A. *Change in ventricular cavity size: differential effects on QRS and T wave amplitude*. Circulation 1985; 72: 495-501.
16. Rautaharju P, Park L, Rautaharju F, Crow R. *A standardized procedure for locating and documenting ECG chest electrode positions*. J Electrocardiol 1998; 31: 17-29.
17. Sokolow M, Lyon T P. *The ventricular complex in left ventricular hypertrophy as obtained by unipolar precordial and limb leads*. Am Heart J 1949; 37: 161-86.
18. Casale P N, Devereux R B, Kligfield P, Eisenberg R R, Miller D H, Chaudhary B S et al. *Electrocardiographic detection of left ventricular hypertrophy: development and prospective validation of improved criteria*. J Am Coll Cardiol 1985; 6: 572-80.
19. Gubner R, Ungerleider H E. *Electrocardiographic criteria of left ventricular hypertrophy*. Arch Intern Med 1943; 72: 196-209.
20. Hall J E. *Guyton et Hall textbook of medical physiology*. 12th ed. Philadelphia, Pa.: Saunders, 2011: 134-135.
21. Lepeschkin E, Surawicz B. *The measurement of the Q-T interval of the electrocardiogram*. Circulation 1952; 6: 378-88.
22. Bazett H C. *An analysis of the time-relations of electrocardiograms*. Heart 1920; 7: 353-70.
23. Madias J E, Bazaz R, Agarwal H, Win M, Medepalli L. *Anasarca-mediated attenuation of the amplitude of electrocardiogram complexes: a description of a heretofore unrecognized phenomenon*. J Am Coll Cardiol 2001; 38: 756-64.
24. Farb A, Devereux R B, Klgfield P. *Day-to-day variability of voltage measurements used in electrocardiographic criteria for left ventricular hypertrophy*. J Am Coll Cardiol 1990; 15: 618-23.
25. Van Den Hoogen J P, Mol W H, Kowsoleea A, Ree J W, Thien T, Van Weel C. *Reproducibility of electrocardiographic criteria for left ventricular hypertrophy in hypertensive patients in general practice*. Eur Heart J 1992; 13: 1606-10.
26. McLaughlin S C, Aitchison T C, Macfarlane P W. *The value of the coefficient of variation in assessing repeat variation in ECG measurements*. Eur Heart J 1998; 19: 342-351.

27. Angeli F, Verdecchia P, Angeli E et al. *Day-to-day variability of electrocardiographic diagnosis of left ventricular hypertrophy in hypertensive patients. Influence of electrode placement.* J Cardiovasc Med 2006; 7: 812-16.

28. Madias J E. *Manual-based versus automation-based measurements of the amplitude of QRS complexes and T waves in patients with changing edematous states: clinical implications.* J Electrocardiol 2008; 41: 15-8.

29. Smit D, de Cock C C, Thijs A, Smulders Y M. *Effects of breath-holding position on the QRS amplitudes in the routine electrocardiogram.* Electrocardiol 2009; 42: 400-4.

30. Hall J E. *Guyton et Hall textbook of medical physiology.* 12th ed. Philadelphia, Pa.: Saunders 2011: 274.

The invention claimed is:

1. A computerized method comprising performing in an ECG apparatus the steps of:

obtaining a first electrocardiography (ECG) reading and a second ECG reading from a test subject such that the first ECG reading and the second ECG reading are obtained using the same electrode positions on the test subject, wherein the first ECG reading comprises a first T wave amplitude reading and the second ECG reading comprises a second T wave amplitude reading, or the first ECG reading comprises a first T/R amplitude ratio and the second ECG reading comprises a second T/R amplitude ratio;

detecting, with the ECG apparatus, whether the first ECG reading and the second ECG reading comprise sets of ECG signals which, based on experimental data, respond to a decrease of blood volume of the test subject by a statistically significant strength decrease, wherein the decrease of blood volume of the test subject is 10% or less of the total blood volume of the test subject;

in response to detecting that the second ECG reading exhibiting a statistically significant strength decrease compared with the first ECG reading and in response to detecting a TV4 amplitude decrease of 70 µV or a TV4/RV4 relation decrease of 10%, raising an alert condition, which indicates potential decrease of blood volume of the test subject; and in response to raising the alert condition, indicating, to a user, the alert condition indicating the potential decrease of the blood volume of the test subject.

2. The method according to claim 1, wherein the ECG signals comprise one or more of TV2, TV3, TV4, TV5, TV6, TII, RV1, RV2, RV3, TV4/RV4 and TV5/RV5.

3. The method according to claim 1, wherein the ECG signals comprise one or more of TV3, TV4, TV5, RV3, TV4/RV4 and TV5/RV5.

4. The method according to claim 2, wherein the ECG signals reading comprise TV4.

5. The method according to claim 1, wherein the method further comprises filtering out spurious anomalies in at least one of the first ECG reading and the second ECG reading.

6. An apparatus comprising:

at least one memory for storing program code instructions and at least one central processing unit for executing the program code instructions;

an electrocardiography (ECG) apparatus for obtaining ECG readings from a test subject;

wherein the program code instructions, when executed by the at least one central processing unit, cause the apparatus to:

obtain a first ECG reading and a second ECG reading from a test subject such that the first ECG reading and the second ECG reading are obtained using the same electrode positions on the test subject, wherein the first ECG reading comprises a first T wave amplitude reading and the second ECG reading comprises a second T wave amplitude reading, or the first ECG reading comprises a first T/R amplitude ratio and the second ECG reading comprises a second T/R amplitude ratio;

detect whether the first ECG reading and the second ECG reading comprise sets of ECG signals which, based on experimental data, respond to a decrease of blood volume of the test subject by a statistically significant strength decrease, wherein the decrease of blood volume of the test subject is 10% or less of the total blood volume of the test subject;

in response to detecting that the second ECG reading exhibits a statistically significant strength decrease compared with the first ECG reading and in response to detecting a TV4 amplitude decrease of 70 µV or a TV4/RV4 relation decrease of 10%, raise an alert condition, which indicates potential decrease of blood volume of the test subject; and in response to raising the alert condition, indicate to a user said alert condition indicating the potential decrease of the blood volume of the test subject.

7. A tangible, non-transitory memory storing program code instructions, wherein the program code instructions, when executed in an electrocardiography (ECG) apparatus, cause the ECG apparatus to perform the steps of:

obtaining a first ECG reading and a second ECG reading from a test subject such that the first ECG reading and the second ECG reading are obtained using the same electrode positions on the test subject, wherein the first ECG reading comprises a first T wave amplitude reading and the second ECG reading comprises a second T wave amplitude reading, or the first ECG reading comprises a first T/R amplitude ratio and the second ECG reading comprises a second T/R amplitude ratio;

detecting whether the first ECG reading and the second ECG reading comprise sets of ECG signals which, based on experimental data, respond to decrease of blood volume of the test subject by a statistically significant strength decrease, wherein the decrease of blood volume of the test subject is 10% or less of the total blood volume of the test subject;

in response to detecting that the second ECG reading exhibiting a statistically significant strength decrease compared with the first ECG reading and in response to detecting a TV4 amplitude decrease of 70 µV or a TV4/RV4 relation decrease of 10%, raising an alert condition, which indicates potential decrease of blood volume of the test subject; and in response to raising the alert condition, indicating, to a user, the alert condition indicating the potential decrease of the blood volume of the test subject.

* * * * *